United States Patent [19]

Reeves et al.

[11] Patent Number: 5,151,321

[45] Date of Patent: Sep. 29, 1992

[54] METHOD OF MAKING CONDUCTIVE, WATER AND/OR ALCOHOL REPELLENT NONWOVEN FABRIC AND RESULTING PRODUCT

[75] Inventors: William G. Reeves, Woodstock; Michael D. Powers, Dunwoody; Michael P. Mathis, Marietta; Leonard E. Duello, Woodstock, all of Ga.

[73] Assignee: Kimberly-Clark Corporation, Neenah, Wis.

[21] Appl. No.: 20,284

[22] Filed: Mar. 2, 1987

Related U.S. Application Data

[63] Continuation-in-part of Ser. No. 645,377, Aug. 29, 1984, abandoned.

[51] Int. Cl.$^5$ .................. B32B 5/26; B32B 27/02; B32B 27/32; B32B 33/00
[52] U.S. Cl. .................. 428/286; 428/288; 428/289; 428/290; 428/296
[58] Field of Search ............ 428/288, 289, 290, 286

[56] References Cited

U.S. PATENT DOCUMENTS

| | | |
|---|---|---|
| 3,728,151 | 4/1973 | Sherman et al. . |
| 3,762,984 | 10/1973 | Goldbeck . |
| 4,041,203 | 8/1977 | Brock et al. ............ 428/296 |
| 4,115,605 | 9/1978 | Hultman et al. . |
| 4,382,990 | 5/1983 | Coates .................... 428/290 |
| 4,393,159 | 7/1983 | Lybrand . |
| 4,419,391 | 12/1983 | Taraka et al. . |
| 4,426,476 | 1/1984 | Chang . |
| 4,668,726 | 4/1987 | Howells ................. 524/225 |

Primary Examiner—James C. Cannon
Attorney, Agent, or Firm—William D. Herrick

[57] ABSTRACT

Improved treatment, composition and method of obtaining a naturally hydrophobic nonwoven web with desired conductivity and/or water repellency, and alcohol repellency. To obtain conductivity, the web is contacted with a composition containing an oxygen or nitrogen rich compound such as ethers, acids or alcohols and especially polymers thereof such as polyethers, and polyacids having an affinity for the substrate. In a further preferred embodiment alcohol repellency is obtained by subsequent or simultaneous contact of the treated web under appropriate pH conditions with a fluorocarbon-containing composition. The result is a conductive material satisfying anti-static requirements for surgical room use and still maintaining desirable water and alcohol repellent properties. Preferred embodiments include treatment with compounds having both moieties as part of the molecule producing a combination of both desired effects. Materials produced in accordance with the invention find applications where ever it is necessary that conductivity eliminate static and that water repellency be achieved. In particular, the materials are useful for surgical applications as gowns, drapes, and the like. Specific examples of treatment compositions include sulfonated polystyrene as a polyacid and ethylene oxide condensates as polyethers, for example. For repellency of fluids having lower surface tension than water, certain fluorocarbons or silicones may be used.

13 Claims, 2 Drawing Sheets

METHOD OF MAKING CONDUCTIVE, WATER AND/OR ALCOHOL REPELLENT NONWOVEN FABRIC AND RESULTING PRODUCT

This application is a continuation-in-part of copending U.S. patent application Ser. No. 645,377 filed 29 Aug. 1984, now abandoned.

BACKGROUND OF THE INVENTION

1. Field of the Invention

The present invention relates generally to the manufacture of nonwoven fabrics and their treatment to impart desired properties. More particularly, it relates to such fabrics that are normally hydrophobic and substantially nonconductive which are desired for applications requiring conductivity and water and/or alcohol repellency. Applications for fabrics with these properties include, but are not limited to, disposable items for surgical room use such as gowns, drapes, table covers and the like. A particular application is in the manufacture of sterilization wrapper used to enclose items to be sterilized and maintain them in a sterilized condition until used. Such nonwovens are manufactured from a wide variety of materials including naturally hydrophobic fibers of synthetic polymers such as polyolefins, polyesters, polyamides, and the like.

2. Description of the Prior Art

The manufacture of nonwoven webs for the above-identified applications is well-known. In addition, it is conventional practice to treat such nonwovens to impart desired properties such as conductivity and water and/or alcohol repellency. For example, U.S. Pat. No. 4,041,203 to Brock and Meitner issued 9 Aug. 1977 describes a nonwoven laminate of a meltblown microfibrous web and a spunbonded web having very desirable attributes for sterilization wrap. The patent describes treatment of such laminates for electrical conductivity and repellency properties with a quaternary ammonium antistatic agent and a high molecular weight cationic fluorocarbon aqueous emulsion fluid repellent. Additional such treatment compositions are described in U.S. Pat. No. 4,115,605 to Hultman and Bergsbaken dated 19 Sep. 1978. This latter patent also discloses benefits of including salts such as lithium chloride in the treatment compositions.

While such treatments have been successful to a significant degree in attaining the intended results, it remains further desired to improve the effectiveness of such treatment and reduce the level of treatment required, all while maintaining or exceeding the conductivity and repellency levels hitherto obtained. In this manner, economy of production as well as product improvements may be obtained.

SUMMARY OF THE INVENTION

In accordance with the present invention, properties such as water repellency/absorbency and surface electrical conductivity of nonwoven webs of naturally hydrophobic fibers are controlled by contacting them with a composition containing a single active compound with a structural combination of conductive and repellent moieties, for example, oxygen or nitrogen-rich compounds with polar groups including certain carboxylic acids, phosphates, sulphates, amines, ammonium salts, polyethers, and polyacids, all having an affinity for the fibers. In general, the molecule of the compound contains an affinity imparting moiety, for example, the above-described polar units, as well as a functional or active moiety unit imparting the desired property, for example a silicone or fluorocarbon imparting repellency. This treatment results in highly efficient distribution of the agents throughout the web, particularly when a dip and squeeze method of application is employed. In most cases, the effectiveness of the treatment is so high that the need for additional conductivity agents is avoided. In spite of the hydrophobic nature of the substrate, there is an unexpectedly strong attraction to the substrate so that a desirable degree of durability of the resulting property is achieved. In all cases, the interaction is such that a high degree of control is afforded in selecting a desired combination of properties such as electrical conductivity and repellency.

While it is not desired to limit the invention to any particular theory, it is believed that the oxygen/nitrogen rich moieties uniquely adhesively attach or orient towards the normally hydrophobic substrates while permitting alignment of the molecules in a manner which passes electrical charge and permits surface electrical conductivity of a relatively permanent nature while also allowing the repellent agent to form a film-like surface coating and impart repellent properties. In general, the repellent moieties are believed to be directed outward forming a filmlike layer while the —O— and —N— moieties are inwardly directed providing ease of electrical charge transfer.

Preferred embodiments include compositions containing molecules from one or more of four classes. First, those where the high affinity moiety is attached to one end of the molecule and the functional or active moiety constitutes the rest. Second, those where the affinity moiety is pendant from the active moiety and is present in polymer form with the functional moiety outside away from the backbone. Third, those where such moieties are on opposite sides of the molecule. Fourth, those where the moieties are both joined internally within a polymeric chain. Other configurations within the scope of the present invention will be apparent to those skilled in this art. It is preferred that the treatment be carried out under controlled pH conditions. The result is a nonwoven web, especially suitable for medical applications and surgical room uses, having controlled and desired levels of conductivity as well as water, and if desired, alcohol repellency. These results are obtained in a highly efficient manner to a degree that permits reduced treatment levels. Examples of nonwoven webs that may be so treated include those described in U.S. Pat. No. 4,041,203 to Brock and Meitner dated 9 August 1977 as well as others manufactured from naturally hydrophobic polyolefins. Specific treating agents and their active moieties include certain quaternary ammonium compounds (quaternary nitrogen), sulfonated polystyrene (sulfonate groups), polyvinyl alcohol (alcohol groups), acrylic acid latexes (carboxylic acid groups), and ethylene oxide condensates (ether oxygens) and related compounds.

DESCRIPTION OF PREFERRED EMBODIMENTS

Figure 1:
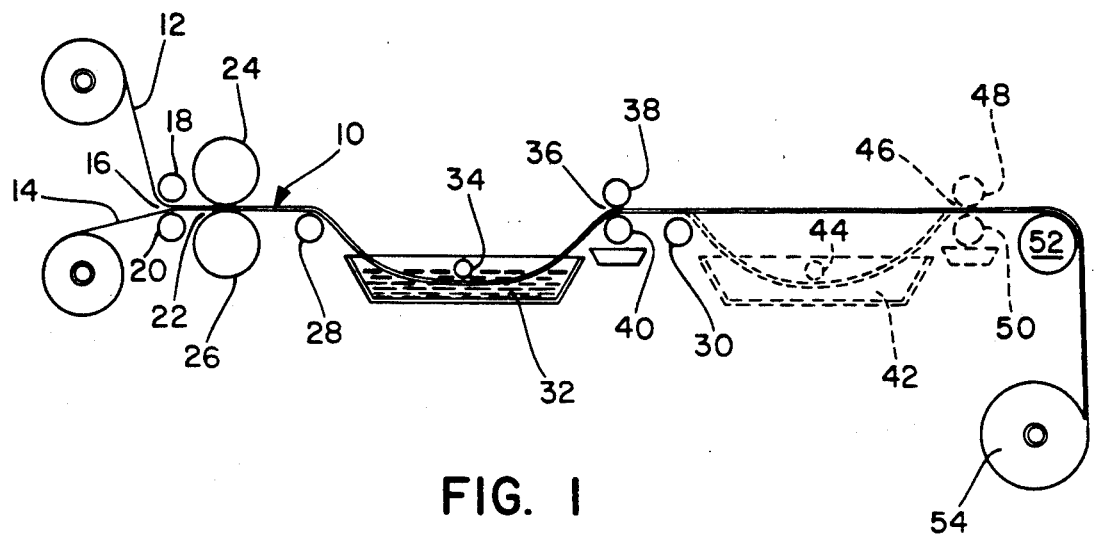
FIG. 1 is a schematic illustration of a process which may be employed in accordance with the invention.

The manufacture of nonwoven webs from naturally hydrophobic polymers by extrusion of fibers or filaments from solvent or melt solutions has become a highly developed art. Examples of such processes are described in U.S. Pat. Nos. 3,338,992 and 3,341,394 to Kinney dated 29 Aug. 1967 and 12 Sep. 1967, respectively, and Levy U.S. Pat. No. 3,276,944 dated 4 Oct. 1966, Hartmann U.S. Pat. No. 3,502,763 dated 24 Mar. 1970 and 3,509,009 dated 28 Apr. 1970 as well as more recently in U.S. Pat. No. 4,340,563 dated 20 Jul. 1982 to Appel and Morman. It is also well-known to form microfibrous webs by meltblowing of naturally hydrophobic thermoplastic polymers, and such is described, for example, in an article entitled "Superfine Thermoplastic Fibers" appearing in *Industrial and Engineering Chemistry*, Vol. 48, No. 8, pp. 1342-1346 which, along with Naval Research Laboratories Report 11437 dated 15 Apr. 1954, describes work done at the Naval Research Laboratories in Washington, D.C. Patent references to such microfibrous materials appear in U.S. Pat. No. 3,715,251 dated 6 Feb. 1973 to Prentice, 3,704,198 dated 28 Nov. 1972 to Prentice, 3,672,242 dated 11 Jul. 1972 to Prentice, and 3,595,245 dated 27 Jul. 1971 to Buntin et al. as well as in the aforementioned U.S. Pat. No. 4,041,203 to Brock and Meitner dated 9 Aug. 1977. The manufacture of the nonwoven webs to be treated in accordance with this invention forms no part of the instant invention, and any of the above-described methods and means may be employed as well as others which will suggest themselves to those skilled in the art. However, the nonwovens described in U.S. Pat. No. 4,041,203 to Brock and Meitner dated 9 Aug. 1977 represent preferred webs for treatment in accordance with the invention and, to the extent this patent describes the manufacture of such fabrics, it is hereby incorporated herein.

Figure 3B:
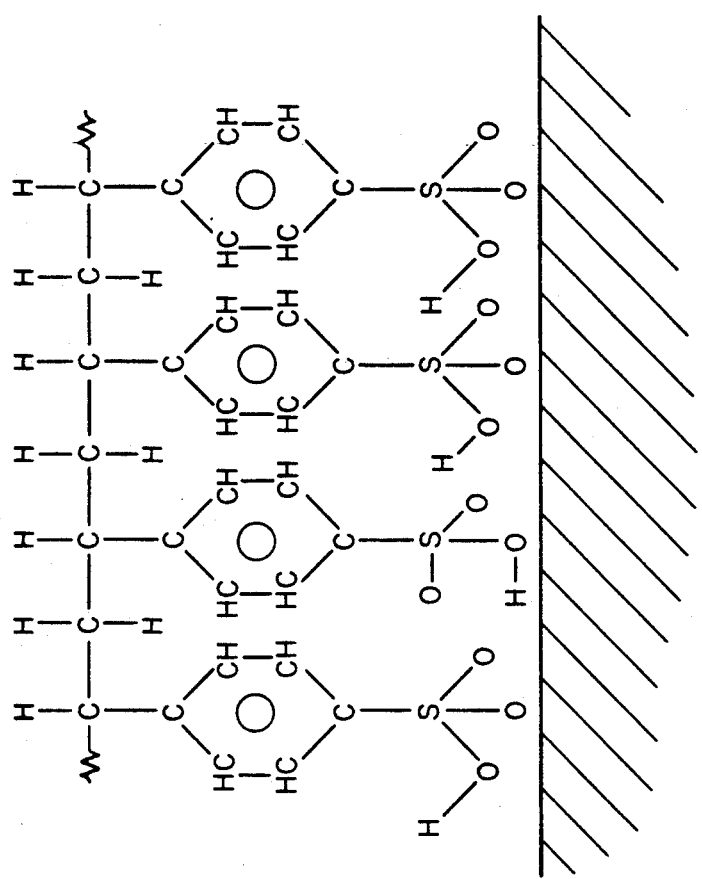
FIGS. 3a and 3b schematically illustrate examples of molecular orientation on a polymer surface.
Figure 3A:
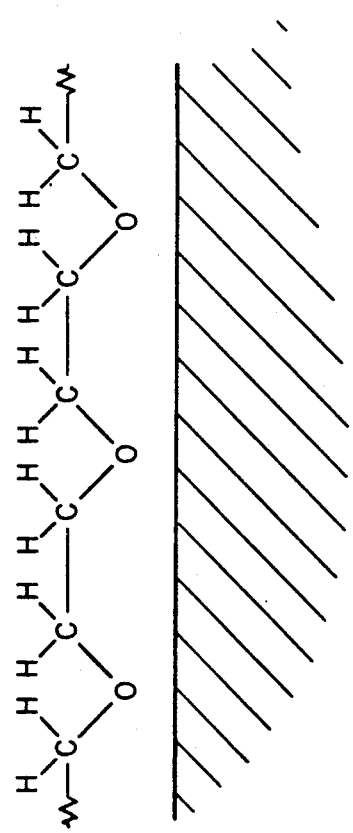

An essential feature of the present invention is the treatment of such nonwoven fabrics to obtain desired properties such as electrical conductivity and repellency. In accordance with the invention, the nonwoven is treated by contact with compounds having moieties with certain polar groups, typically those rich in oxygen and/or nitrogen. By "conductivity property" it is meant that the web, after treatment, has an electrical conductivity of about 0.5 sec. or less as measured by the static decay test (Federal Test Method 101C) which measures the time to dissipate a 5000 v charge to less than 500 v. By "oxygen and/or nitrogen rich" it is meant that the compositions contain a compound that is a polymeric material having pendant oxygen or nitrogen groups on one side of the molecule or repeating units of the polymer backbone, for example, certain carboxylic acids, phosphates, sulphates, amines and ammonium salts. These oxygen/nitrogen-rich moieties surprisingly interact strongly with the hydrophobic surface, orienting the molecules so that the polar moieties of the polymer backbone form a layer attached to the polyolefin surface, effectively bonding to it. FIGS. 3a and 3b schematically illustrate this effect with oxygenated compounds on a polymer surface, in this case polypropylene. As shown, with structural details omitted for clarity, the oxygen atoms interact with the polymer surface, and the moieties on the opposite side of the backbone extend away from and form a generally continuous layer above the polymer surface. The nature of the resulting layer determines the effective surface characteristics of the fiber making up the web surface: if the moiety facing out from the surface is a fluorocarbon, the fiber will behave as alcohol repellent; if the moiety facing out is a hydrocarbon, the fiber will behave as water repellent; and if the moiety facing out is water wetting, the fiber will behave as an absorbent medium. An additional result of the orientation of oxygen/nitrogen-rich moieties on the surface of polyolefin fibers is that it permits control of the surface electrical resistivity, irrespective of the repellent/absorbent nature of the upper layer. The preferred conductive agents will depend upon the nature and composition of the nonwoven material. However, for example, when the nonwoven comprises a laminate of spunbonded and meltblown polypropylene as described in U.S. Pat. No. 4,041,203 to Brock and Meitner dated 9 Aug. 1977, preferred highly oxygenated compounds include ethylene oxide condensates, or polyacids such as poly(p-styrene sulfonic acid). Preferred highly nitrogenated compounds include polyamines and quaternary ammonium compounds.

In accordance with a further preferred embodiment of the present invention, when it is desired to impart electrical conductivity or a desired degree of repellency, the nonwoven web is treated under controlled pH conditions. By "controlled pH" it is meant that the repellent moiety does not interfere with or is not, itself, interfered with by the conductive agent. Species such as carboxylic acids and amines which form salts must be applied under pH conditions where such salts are not formed, e.g. in a neutral state. In other cases using acid moieties, for example, an acid pH will be preferred while those using base moieties will achieve best results under chemically basic conditions. Examples 1 and 2 below demonstrate an embodiment where the desired property will determine the pH conditions with an electrically conductive product obtained under acidic conditions and an electrically nonconductive product obtained under neutral conditions. Examples 7 and 8 below demonstrate an embodiment where the desired property will determine the pH conditions with a repellent product obtained under neutral conditions and a wettable product obtained under acidic conditions.

The generalized structures of the compounds for each of the above identified four classes providing conductive and/or repellent properties are as follows ("F" indicates active or functional moiety and "A" indicates attaching moiety):

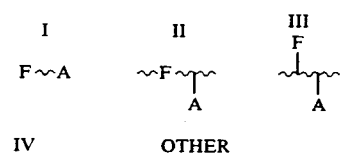

| I | II | III | IV |
|---|---|---|---|
| Alkaquat DMB-ST | Versa TL 121 Polyacids | Methyl acrylate latices | Cordova XA 1007 Corcat P-12 |
| Triton X-200 | Polyalcohols | Silicones | ETO Condensates |
| Arko Stat EX 223 | Vinol 125 Carbopol 934 | | Carbowax 300 or 20 |

OTHER: ~F—A~ As defined by examples below.

Examples of compositions falling within each of these classes are listed below.

| I | II | III | IV |
|---|---|---|---|
| | | | Triton X-200 |
| | | | Emulphor 980 |
| | | | Igepal CO-970 |
| | | | Tween 20 |
| | | | Pluronic F68 |

In a particularly preferred embodiment especially for treating nonwovens of the type described in U.S. Pat. No. 4,041,203 to Brock and Meitner dated 9 Aug. 1977, preferred compositions include sulfonated polystyrenes and quaternary ammonium compounds. In embodiments of this invention, it is necessary only to treat the nonwoven web with a single composition under appropriate pH conditions to obtain the benefits of the present invention.

The level of treatment required in accordance with the present invention will depend on the desired levels of conductivity and repellency as well as the nature and basis weight of the nonwoven web being treated as well as on the application means. In general, while the basis weight may vary widely, it is contemplated that webs treated in accordance with the invention will have basis weights generally in the range of up to about 5 oz/yd$^2$ and, preferably, 0.5 oz/yd$^2$ to 2.0 oz/yd$^2$. For surgical applications, conductivity requirements are discharge of 5000 v to 500 v in less than 0.5 sec. as set forth in NFPA (National Fire Protection Association) Book 56. Repellency properties for surgical applications will be in the range of from about 15 to 100 in hydrohead, preferably 25 to 60 in hydrohead for water as measured by hydrostatic head test AATCC Test Method 127-1977; about 1 to 5, preferably 3 to 5 for alcohol as measured by static drop test using 70% isopropyl alcohol in water as described by 3M Corporation, Scotch Ban Product Manual. However, it is a feature of the present invention that single compounds can be used to replace combinations of compounds while obtaining desired results and economies of manufacture.

Various methods are employed for contacting the nonwoven web with the treatment composition or compositions in accordance with the invention. For example, the material may be printed on by means of print rolls or other coating steps, or saturation techniques may be employed. Preferably, the composition or compositions may be applied by running the web into a bath of the treatment composition or compositions and removing excess by application of pressure and squeeze rolls. This dip and squeeze process, in general, results in more uniform distribution of the agent throughout the web and permits higher levels to be attained at faster operating speeds if desired. Turning to FIG. 1, a representative process for carrying out the invention will be described. As illustrated, a nonwoven web 10 may be formed in the manner described in U.S. Pat. No. 4,041,203 to Brock and Meitner dated 9 Aug. 1977 by combining meltblown web 12 with spunbonded web 14 in nip 16 between compacting rolls 18 and 20. Web 10 may then be pattern bonded at nip 22 between pattern roll 24 and anvil roll 26 and controlled by guide roll 28. After bonding, the web 10 is then directed to bath 32 under support member 34, and excess treatment composition is removed by passage through a squeeze nip 36 formed by rolls 38 and 40. If two treatment compositions are employed, the dip and squeeze may be repeated as shown in phantom lines by directing over guide roll 30 to bath 42, support member 44, and squeeze nip 46 formed by rolls 48 and 50. Also the web is then preferably heated to a temperature of about 220° F. to 300° F., preferably 270° F. to 290° F. for polypropylene by passage over heated drum 52 to set the repellent composition and complete drying. The drying temperatures for other polymers will be apparent to those skilled in the art. Thus treated web 54 may then be converted directly into sheets such as sterile wrappers or the like or may be stored for further use or conversion.

Figure 2:
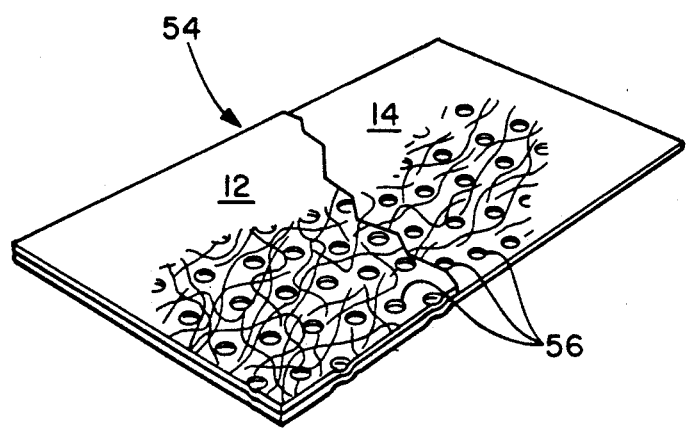
FIG. 2 illustrates in schematic perspective a web treated in accordance with the invention.

FIG. 2 illustrates schematically a thus treated web 54 comprising meltblown layer 12 and spunbonded layer 14 united by a pattern of spaced embossments 56. It will be apparent that the bonding means is illustrative only, and other means for combining the web may be employed, such as heat activation of thermoplastic fibers, adhesives, and the like. Of course, where a single web is treated, no lamination will be required, although, as is well-known, some bonding means may still be desired.

FIGS. 3a and 3b illustrate the molecular orientation of oxygen-rich molecules toward the polymer, in this case polypropylene, surface which is shown as crosshatched. The drawing is obviously schematic in nature, and details of the molecules have been omitted for clarity. As shown, the oxygen atoms tend to adhere to the polymer surface, thus leaving the polymer backbone to form a layer above the polymer surface.

EXAMPLES

The following examples illustrate the ability to change the interactive and the active moieties of compounds in such a manner so as to produce fabric which is electrically conductive and hydrophobic. Finer control of the surface properties are also illustrated through the use of preferred treatment compositions applied under controlled pH conditions and through control of the spacing of the interactive moieties by proper selection of compound construction.

Example 1 (Class II)

A treatment solution was prepared by diluting 80 gm. of Versa TL-121 (a p-sulfonated polystyrene, National Starch & Chemical) to 4,000 ml. with distilled water. To this solution was added, with stirring, 24 gm. of 1-hexanol (J. T. Baker) as a wetting aid and 1 ml. of 1-octanol (Fisher Chemical) as a foam suppressant. The pH of the resulting solution was between 2 and 3.

A polypropylene fabric made by laminating 0.325 oz/yd$^2$ spunbond fibers to both sides of a 0.75 oz/yd$^2$ meltblown fiber mat (total fabric weight=1.4 oz./yd$^2$) was saturated with the above mentioned treatment solution, and excess solution was squeezed out to provide a total pickup of 118%. The web fabric was dried in a hot air oven at 120° C. for 10 minutes.

The fabric was tested for water repellency with a static drop test. This test was performed by placing a drop of distilled water slightly smaller than a dime on the fabric surface and observing whether or not the drop was absorbed. Any fabric which did not wet within 10 seconds was rated repellent. The fabric prepared as described above was rated repellent using this test.

Static discharge properties were measured using a static decay meter and procedure as described in NFPA 56A. In this test a charge of 5000 v is applied to the fabric and the time required to discharge to 500 v is recorded. Times of less than 0.5 sec. are considered passing. Using this test, the fabric prepared as described above had an average discharge time of 0.11 sec.

Without limiting the scope of the invention, the following is offered as an explanation of how the invention may produce the desired surface properties. In this example the interactive moiety chosen is the oxygen rich sulfonate moiety and the active group is polystyrene. The sulfonate moiety is electrically conductive at this pH and hydrophilic. The hydrophilic, sulfonate moiety unexpectedly and preferentially attaches, or orients, to the hydrophobic surface of the nonwoven and is covered by the polystyrene moiety. The polystyrene moiety is of sufficient hydrophobicity and size to cover the hydrophilic nature of the sulfonate moiety. The resultant treated fabric is electrically conductive and hydrophobic.

This example illustrates the ability to control the nonwoven surface so as to produce an electrically conductive, hydrophobic surface using a compound consisting of a multitude of identical oxygen rich moieties which unexpectedly attach, or orient, onto a hydrophobic nonwoven surface and are covered by the compound's active moiety which is sufficiently strong in hydrophobicity and size to render the resultant fabric hydrophobic.

Example 2 (Class II)

A two liter aliquot was taken from the treatment solution of Example 1 and its pH was adjusted to 7. When fabric of the type used in Example 1 was treated as in Example 1 (wet pickup=114%), the resulting fabric was judged repellent using the static drop test, but would not accept the required 5000 volts which is needed to perform the electrical conductivity test.

Without limiting the scope of the invention, the following is offered as an explanation of how the invention may produce the chosen surface properties. In this example the interactive oxygen rich moieties, sulfonate groups, have been deactivated due to the increased pH and are therefore electrically nonconductive. The hydrophilic sulfonate moieties still unexpectedly and preferentially attach, or orient, to the hydrophobic surface of the nonwoven and are still covered by the polystyrene moiety. The hydrophobicity of the polystyrene moiety has not been affected by the pH change and still covers the hydrophilic nature of the sulfonate moieties. The resultant treated fabric is electrically nonconductive and hydrophobic.

This example illustrates the importance of controlling the pH of a treatment solution, such as that of Example 1, so as to produce the desired properties, an electrically conductive, hydrophobic fabric instead of an electrically nonconductive, hydrophobic fabric.

Example 3 (Monomer of Class II)

As in Example 1 above, except that 24 grams of p-toluene sulfonic acid (reagent grade, Eastman Kodak Chemicals) were substituted for Versa TL-121. The pH of the resulting solution was 2. When fabric of the type used in Example 1 was treated as in Example 1 (wet pickup= 101%), the resulting fabric was judged repellent using the static drop test of Example 1 and would not pass the electrical conductivity test.

Without limiting the scope of the invention, the following is offered as an explanation of how the invention may produce the chosen surface properties. In this example the interactive moiety chosen is the oxygen rich sulfonate moiety and the active group is toluene. The control over spacing of the sulfonate moiety is lost for p-toluene sulfonic acid (PTSA) as compared with Versa TL-121, this probably adversely affects the electrical conductivity of a laminate treated with the PTSA. The hydrophilic, sulfonate moiety of the PTSA unexpectedly and preferentially attaches, or orients to the hydrophobic surface of the nonwoven and is covered by the toluene moiety. The toluene moiety is of sufficient hydrophobicity and size to cover the hydrophilic nature of the sulfonate moiety. The resultant treated fabric is electrically nonconductive and hydrophobic.

This example illustrates the importance of controlling the spacing of the interactive moieties on the nonwoven surface through the proper choice of molecular structure of a treating compound, such as that used in Example 1, so as to produce the desired properties, an electrically conductive, hydrophobic fabric instead of an electrically nonconductive hydrophobic fabric.

Example 4 (Class I)

As in Example 1 above, except that 30 grams of Arko Stat EX 223 (monococo, trimethyl quaternary ammonium compound, Arkansas Chemical Co., also known as Adogen 461, Sherex Chemical Co.) were substituted for Versa TL-121. The pH of the resulting solution was 4–5. When fabric of the type used in Example 1 was treated as described in Example 1 (wet pickup=100%), the treated fabric was rated as repellent using the static drop test of Example 1 and it discharged 5000 volts to 500 volts at the limit of the measurement of the machine, 0.03 seconds.

Without limiting the scope of the invention, the following is offered as an explanation of how the invention may produce the desired surface properties. In this example the interactive moiety chosen is the nitrogen rich quaternary ammonium moiety and the active moiety is a coco-lengthed hydrocarbon chain. The quaternary ammonium moiety is electrically conductive and hydrophilic. The quaternary ammonium moiety unexpectedly and preferentially attaches, or orients, to the hydrophobic surface of the nonwoven and is covered by the coco-lengthed hydrocarbon moiety. The hydrocarbon moieties are of sufficient hydrophobicity and size to cover the hydrophilic nature of the quaternary ammonium nitrogen moiety. The resultant treated fabric is electrically conductive and hydrophobic.

This example illustrates that the ability to control the nonwoven surface so as to produce an electrically conductive, hydrophobic surface, as in Example 1, is not limited to an oxygen rich compound but can also be accomplished with a nitrogen rich compound if it contains an active moiety sufficiently strong in hydrophobicity and size to render the resultant fabric hydrophobic.

Example 5 (Class I)

As in Example 1, except that 40 grams of Alkaquat DMB-ST (benzyl dimethyl stearyl ammonium chloride, Alkaril Chemicals Inc.) were substituted for Versa TL-121. The pH of the resulting solution was 5–6. When fabric of the type used in Example 1 was treated as described in Example 1 (wet pickup 100%), the treated fabric was rated as repellent and it discharged 5000 volts to 500 volts in 0.48 seconds.

Without limiting the scope of the invention, the following is offered as an explanation of how the invention may produce the desired surface properties. In this example the interactive moiety chosen is the nitrogen rich, quaternary ammonium moiety and the active moieties are stearyl and benzyl groups. The quaternary ammonium moiety is electrically conductive at this pH and hydrophilic. The quaternary ammonium moiety unexpectedly and preferentially attaches, or orients, to the hydrophobic surface of the nonwoven and is covered by the stearyl and benzyl active moieties. The active moieties are of sufficient hydrophobicity and size to cover the hydrophilic nature of the quaternary ammonium moiety. The resultant treated fabric is electrically conductive and hydrophobic.

This example illustrates that the ability to control the nonwoven surface so as to produce an electrically conductive, hydrophobic surface, using the interactive moiety of Example 4, is not limited to the use of a particular active moiety as long as it is sufficiently strong in hydrophobicity and size to render the resultant fabric hydrophobic.

Example 6 (Class Other)

As in Example 1 above, except that 15 grams of Drustat 75 (amido quaternary ammonium sulfate, PVO International Inc.) were substituted for Versa TL-121. The pH of the solution was adjusted to 2-3. When fabric of the type used in Example 1 was treated as in Example 1 (wet pickup=114%), the resulting fabric was judged repellent using the static drop test and discharged the 5000 volts to 500 volts in 0.17 seconds.

Without limiting the scope of the invention, the following is offered as an explanation of how the invention may produce the desired surface properties. In this example the interactive moieties chosen are the amido and quaternary ammonium groups. The active groups are the unspecified aliphatic groups of the amido and quaternary ammonium groups. The quaternary ammonium moiety and the amido moiety are electrically conductive at this pH and hydrophilic. The amido group and the quaternary ammonium group unexpectedly and preferentially attach, or orient, to the hydrophobic surface of the nonwoven fabric and the rest of the molecule, the active moieties, orients on top of the two interactive moieties. The sum of the hydrophobic nature of the active moieties covers the hydrophilic nature of the two interactive groups. The resultant fabric is electrically conductive and hydrophobic.

This examples illustrates that the ability to control the nonwoven surface so as to produce an electrically conductive, hydrophobic surface as in Example 4, is not limited to the use of a homogeneous interactive moieties in that an interactive moiety may contain both oxygen and nitrogen atoms.

Example 7 (Class Other)

As in Example 1 above, except that 20 grams of Alkaquat O (1-methyl-1-alkylkamido-ethyl-2-alkylimidazolinium, Alkaril Chemical Co.) were substituted for Versa TL-121. The pH of the resulting solution was 6. When fabric of the type used in Example 1 was treated as in Example 1 (wet pickup=121%), the resulting fabric was judged repellent using the static drop test and discharged the 5000 volts to 500 volts in 0.04 seconds.

Without limiting the scope of the invention, the following is offered as an explanation of how the invention may produce the desired surface properties. In this example the interactive moieties chosen are the amido and quaternary ammonium groups. The active groups are the unspecified aliphatic groups of the amido and quaternary imidazoline groups. The quaternary ammonium moiety is electrically conductive at this pH and hydrophilic. Despite the complexity of the interactive quaternary ammonium moiety, the amido group and the quaternary nitrogen group unexpectedly and preferentially attach, or orient, to the hydrophobic surface of the nonwoven fabric and are covered by the rest of the hydrophobic ring system and the unspecified active moiety of the amido group. The active moieties are sufficiently hydrophobic to cover the hydrophilic nature of the quaternary ammonium group and the resultant fabric is electrically conductive and hydrophobic.

This example illustrates that the ability to control the nonwoven surface so as to produce an electrically conductive, hydrophobic surface as in Example 6, is not limited to simple aliphatic or aromatic active moieties which have free ends but that they may be joined to form a complex ring system which contains the interactive moiety.

Example 8 (Class Other)

A two liter aliquot was taken from the treatment solution of Example 7 and its pH was adjusted to 4. When fabric of the type used in Example 1 was treated as in Example 1 (wet pickup 121%), the resulting fabric was judged absorbent using the static drop test and discharged 5000 volts to 500 volts in 0.07 seconds.

Without limiting the scope of the invention, the following is offered as an explanation of how the invention may produce the chosen surface properties. In this example the interactive moieties chosen are the amido and quaternary ammonium nitrogen groups. The active groups are the unspecified aliphatic groups of the amido and quaternary imidazoline ammonium nitrogen groups. The decrease in pH has significantly strengthened the hydrophilicity of the interactive moieties without affecting their electrical conductivity. The decrease in pH has not affected the unexpected, preferential attachment, or orientation, of the interactive moieties to the hydrophobic surface of the nonwoven fabric. The hydrophobic active moieties orient over the interactive moieties. The change in pH has not increased the strength of the hydrophobicity of the active moieties and the resultant fabric is electrically conductive and hydrophilic.

This example illustrates the importance of controlling the pH of a treatment solution, such as that of Example 7, so as to produce the desired properties, an electrically conductive, hydrophobic fabric instead of an electrically conductive, hydrophilic fabric.

Example 9 (Class I and IV)

As in Example 1 above, except that 20 grams of Triton X-200 (sodium salt of an alkyl aryl polyether sulfonate, Rhom and Haas Co.) were substituted for Versa TL-121. The pH of the resulting solution was 6-7. When fabric of the type used in Example 1 was treated as in Example 1 (wet pickup=109%), the resulting fabric was judged repellent using the static drop test and discharged the 5000 volts to 500 volts in 0.29 seconds.

Without limiting the scope of the invention, the following is offered as an explanation of how the invention may produce the desired surface properties. The compound of this example has two interactive oxygen rich moieties, a sulfonate group and the ether oxygens of the ethoxy groups. The sulfonate group is electrically conductive, the ether oxygens are electrically nonconductive and both groups are hydrophilic. The hydrophobic, active moieties of the compound are the alkyl and aryl groups connected to the sulfonate moiety and the ethylene groups connected to the ether oxygens. Both of the hydrophilic, interactive moieties unexpectantly and preferentially attach, or orient, to the hydrophobic surface of the nonwoven and are covered by the active moieties of the compound. The active moieties are sufficiently hydrophobic to cover the hydrophilic nature of the sulfonate group and ether oxygens. The resultant treated fabric is electrically conductive and hydrophobic.

This example illustrates that the ability to control the nonwoven surface so as to produce an electrically conductive, hydrophobic surface, as in Example 1, is not limited to homogeneous, interactive moieties of similar composition in that the interactive moieties can contain dissimilar atoms as well as the nitrogen or oxygen atom(s).

The following examples illustrate the generality of the attachment, or orientation, and subsequent alignment process illustrated by the compositions in the above examples. In the following examples however all of the treatment compositions produce fabrics which are electrically nonconductive due either to the fact that the interactive moieties are electrically nonconductive or that the active moieties deactivate the electrically conductive interactive moiety.

Example 10 (Class II)

As in Example 1 above, except that 20 grams of Vinol 125 (polyvinyl alcohol, Air Products and Chemicals Inc.) were substituted for Versa TL-121. The pH of the resulting solution was 4. When fabric of the type used in Example 1 was treated as in Example 1 (wet pickup=114%), the resulting fabric was judged repellent using the static drop test and failed the electric conductivity test.

Without limiting the scope of the invention, the following is offered as an explanation of how the invention may produce the chosen surface properties. In this example the interactive moieties chosen are a multitude of oxygen rich alcohol groups and the active group is a polyethylene hydrocarbon chain. The alcohol moieties are electrically nonconductive at this pH and hydrophilic. The hydrophilic, alcohol moieties unexpectedly and preferentially attach, or orient, to the hydrophobic surface of the nonwoven and are covered by the polyethylene hydrocarbon moiety. The polyethylene hydrocarbon moiety is of sufficient hydrophobicity and size to cover the hydrophilic nature of the alcohol moieties. The resultant treated fabric is electrically nonconductive and hydrophobic.

This example illustrates the ability to control the nonwoven surface so as to produce a nonconductive, hydrophobic surface using a compound consisting of a multitude of oxygen rich moieties pendant off a hydrocarbon hydrophobic moiety, where the interactive moieties unexpectedly attach, or orient, to a hydrophobic nonwoven surface and are covered by the active moiety which is sufficiently strong in hydrophobicity to render the resultant fabric hydrophobic.

Example 11 (Class II)

As in Example 10 above, except that 20 grams of Carbopol 934 (acrylic acid polymer, B.F. Goodrich Co.) were substituted for Vinol 125. The pH of the resulting solution was 4. When fabric of the type used in Example 1 was treated as in Example 1 (wet pickup=167%), the resulting fabric was judged repellent using the static drop test and failed the electrical conductivity test.

Without limiting the scope of the invention, the following is offered as an explanation of how the invention may produce the chosen surface properties. In this example the interactive moieties chosen are a multitude of oxygen rich carboxylic acid groups and the active group is a polyethylene hydrocarbon chain. The carboxylic acid moieties of this compound are electrically nonconductive at this pH and hydrophilic. The hydrophilic, carboxylic acid moieties unexpectedly and preferentially attach, or orient, to the hydrophobic surface of the nonwoven and are covered by the polyethylene hydrocarbon moiety. The polyethylene hydrocarbon moiety is of sufficient hydrophobicity and size to cover the hydrophilic nature of the carboxylic acid moieties. The resultant treated fabric is electrically nonconductive and hydrophobic.

This example illustrates that the ability to control the nonwoven surface so as to produce a nonconductive, hydrophobic surface as in Example 10, is not limited to a compound with pendant alcohol interactive groups off a hydrophobic active backbone but can vary in carbon and oxygen content.

Example 12 (Class IV)

As in Example 10 above, except that 20 grams of Carbowax 300 (polyethylene glycol, MW=300; Union Carbide Corporation) were substituted for the Vinol 125. The pH of the resulting solution was 6-7. When fabric of the type used in Example 1 was treated as in Example 1 (wet pickup=116%), the resulting fabric was judged repellent using the static drop test and failed the electrical conductivity test.

Without limiting the scope of the invention, the following is offered as an explanation of how the invention may produce the chosen surface properties. In this example the interactive moieties chosen are a multitude of oxygen rich, ether oxygens and the active moieties are a multitude of saturated ethylene units. The ether oxygens are electrically nonconductive at this pH and hydrophilic. The hydrophilic, ether oxygen moieties unexpectedly and preferentially attach, or orient, to the hydrophobic surface of the nonwoven and are covered by the ethylene moieties. The saturated ethylene moieties are of sufficient hydrophobicity and size to cover the hydrophilic nature of the ether oxygen moieties. The resultant treated fabric is electrically nonconductive and hydrophobic.

This example illustrates that the ability to control the nonwoven surface so as to produce a nonconductive, hydrophobic surface as in Example 10 is not limited to the use of a molecule constructed of an active moiety with pendant interactive moieties.

Example 13 (Class IV)

As in Example 12 above, except that 20 grams of Carbowax 20M (polyethylene glycol, MW=20,000; Union Carbide Corporation) were substituted for Carbowax 300. The pH of the resulting solution was 6-7. When fabric of the type used in Example 1 was treated as in Example 1 (wet pickup=118%), the resulting fabric was judged repellent using the static drop test and failed the electrical conductivity test.

Without limiting the scope of the invention, the following is offered as an explanation of how the invention may produce the chosen surface properties. In this example the interactive moieties chosen are a multitude of oxygen rich, ether oxygens and the active moieties are a multitude of saturated ethylene units. The ether oxygens are electrically nonconductive at this pH and hydrophilic. The hydrophilic, ether oxygen moieties unexpectedly and preferentially attach, or orient, to the hydrophobic surface of the nonwoven and are covered by the ethylene moieties. The saturated ethylene moieties are of sufficient hydrophobicity and size to cover the hydrophilic nature of the ether oxygen moieties. The resultant treated fabric is electrically nonconductive and hydrophobic.

This example illustrates that the ability to control the nonwoven surface so as to produce a nonconductive, hydrophobic surface as in Example 12 is not limited by the molecular weight of the treating compound.

Example 14 (Class IV)

As in Example 12 above, except that separate treatment compositions were prepared at a concentration of 20 grams per four liters containing Pluronic F68 (a block copolymer of propylene oxide and ethylene oxide, BASF Wyandotte Corporation), Emulphor 980 (a polyoxyethylated vegetable oil, GAF Corporation), Igepal CO-970 (nonylphenoxy poly(ethyleneoxy) ethanol, GAF Corporation) and Tween 20 (poly(oxyethylene) 20 sorbitan monolaurate). The pH of the resulting solutions were 6–7. When fabric of the type used in Example 1 was treated as in Example 1 (wet pickups = 100 to 120%), the resulting fabrics were judged repellent using the static drop test and they all failed the electrical conductivity test.

Without limiting the scope of the invention, the following is offered as an explanation of how the invention may produce the chosen surface properties. In this example the interactive moieties chosen are a number of oxygen rich, ether oxygens and the active moieties are a number of saturated ethylene or propylene units plus the head groups of each of the compounds of this example. The oxygens are electrically nonconductive at this pH and hydrophilic. The hydrophilic, ether oxygen moieties unexpectedly and preferentially attach, or orient, to the hydrophobic surface of the nonwoven and are covered by the active moieties. The saturated ethylene moieties and the head groups of the compounds are of sufficient combined hydrophobicity and size to cover the hydrophilic nature of the ether oxygen moieties. The resultant treated fabric is electrically nonconductive and hydrophobic.

This example illustrates that it is not necessary to have a specific head group as long as the head group is nonconductive so as to produce a nonconductive, hydrophobic fabric as in Example 12.

Example 15 Class IV)

As in Example 12 above, except that 20 grams of XA-1007 (polyethylenimine, MW=300; Cordova Chemical Company of Michigan) were substituted for the Carbowax 300. The pH of the resulting solution was 10. When fabric of the type used in Example 1 was treated as in Example 1 (wet pickup = 109%), the resulting fabric was judged repellent using the static drop test and failed the electrical conductivity test.

Without limiting the scope of the invention, the following is offered as an explanation of how the invention may produce the chosen surface properties. In this example the interactive moieties chosen are a multitude of nitrogen rich, imine nitrogens and the active moieties are a multitude of saturated ethylene units. The ratio of primary:secondary:tertiary nitrogens is about 1:1:1. The imine nitrogens are electrically nonconductive at this pH and hydrophilic. The hydrophilic, imine nitrogen moieties unexpectedly and preferentially attach, or orient, to the hydrophobic surface of the nonwoven and are covered by the ethylene moieties. The saturated ethylene moieties are of sufficient hydrophobicity and size to cover the hydrophilic nature of the imine nitrogen moieties. The resultant treated fabric is electrically nonconductive and hydrophobic.

This example illustrates that the ability to control the nonwoven surface so as to produce a nonconductive, hydrophobic surface as in Example 12 is not limited to the use of a molecule constructed of an oxygen containing interactive moiety.

Example 16 Class IV)

As in Example 15 above, except that 20 grams of Corcat P-12 (polyethylenimine, MW=1200; Cordova Chemical Company of Michigan) were substituted for XA-1007. The pH of the resulting solution was 10. When fabric of the type used in Example 1 was treated as in Example 1 (wet pickup=126%), the resulting fabric was judged repellent using the static drop test and failed the electrical conductivity test.

Without limiting the scope of the invention, the following is offered as an explanation of how the invention may produce the chosen surface properties. In this example the interactive moieties chosen are a multitude of nitrogen rich, imine nitrogens and the active moieties are a multitude of saturated ethylene units. The ratio of primary:secondary:tertiary nitrogens is about 1:1:1. The imine nitrogens are electrically nonconductive at this pH and hydrophilic. The hydrophilic, imine nitrogen moieties unexpectedly and preferentially attach, or orient, to the hydrophobic surface of the nonwoven and are covered by the ethylene moieties. The saturated ethylene moieties are of sufficient hydrophobicity and size to cover the hydrophilic nature of the imine nitrogen moieties. The resultant treated fabric is electrically nonconductive and hydrophobic.

The example illustrates that the ability to control the nonwoven surface so as to produce a conductive, hydrophobic surface as in Example 15 is not limited by the molecular weight of the treating compound.

As demonstrated by the examples, the polar groups when applied under controlled pH conditions, form a conductive layer eliminating static charge problems typically associated with polymers such as polypropylene. This is achieved without necessitating addition of a metal and in a manner that can produce a wettable surface if desired. On the other hand, a conductive, fluid repellent surface can also be produced for use as a surgeon's gown material. The invention provides controlled surface properties in a single and efficient treatment step. Moreover, the attraction of the treatment of the surface can be selected to provide properties of increased durability when compared with conventional treatments.

Thus, it is apparent that there has been provided, in accordance with the invention, a treatment composition and method that fully satisfy the objects, aims, and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications, and variations as fall within the spirit and broad scope of the appended claims.

We claim:

1. Method of altering the alcohol and/or water repellent and/or electrical conductive functional properties of a nonwoven fabric comprising polypropylene-containing thermoplastic fibers or filaments comprising the steps of:
   a) providing a wet treatment composition containing a polymer molecule having a combination of functional moieties and oxygen-rich or nitrogen-rich moieties having high affinity for polypropylene wherein either or both of the moieties are free to re-orient with respect to each other, and
   b) contacting said fabric with said composition under pH conditions where said high affinity moieties orient towards and interact with the polypropylene fiber or filament surfaces and molecularly attach to said fabric and said functional moieties orient outward forming a substantially continuous coating.

2. The method of claim 1 wherein said functional moieties are fluorocarbons or silicones and said nonwoven fabric is made alcohol repellent.

3. The method of claim 1 wherein said functional moieties are hydrocarbons and said nonwoven fabric is made water repellent.

4. The method of claim 1 wherein said functional moieties are water wetting and said nonwoven fabric is made water absorbent.

5. The method of claim 1 wherein said high affinity moieties are selected from a group consisting of carboxylic acid moieties, ethylene oxide condensate moieties, polyacid moieties, polyamine moieties, and quaternary ammonium moieties.

6. The method of claim 1 wherein the nonwoven fabric is a laminate of spunbonded and meltblown component layers.

7. A nonwoven fabric comprising polypropylene-containing thermoplastic fibers or filaments and having a substantially continuous coating containing a polymer molecule having a combination of functional moieties and moieties having high affinity of polypropylene wherein the high affinity moieties are oriented towards and molecularly attached to the polypropylene fiber or filament surface of said fabric and said functional moieties are oriented outward forming the substantially continuous coating and imparting a desired alcohol and/or water repellent and/or electrical conductivity functional property to the nonwoven fabric.

8. The nonwoven fabric of claim 7 wherein said functional moieties are fluorocarbons or silicones and said nonwoven fabric is alcohol repellent.

9. The nonwoven fabric of claim 7 wherein said functional moieties are hydrocarbons and said nonwoven fabric is water repellent.

10. The nonwoven fabric of claim 7 wherein said functional moieties are water wetting and said nonwoven fabric is water absorbent.

11. The nonwoven fabric of claim 7 wherein said high affinity moieties are selected from the group consisting of carboxylic acid moieties, ethylene oxide condensate moieties, polyacid moieties, polyamine moieties, and quaternary ammonium moieties.

12. The nonwoven fabric of claim 7 wherein said nonwoven fabric is a laminate of spunbonded and meltblown component layers.

13. The nonwoven fabric of claim 7 wherein the functional properties include hydrohead water repellency within a range of from about 25 to 60 cm, alcohol static drop tests within the range of from about 3 to 5, and static decay results less than about 0.5 second.

* * * * *